(12) United States Patent
Belmonte et al.

(10) Patent No.: US 7,005,011 B2
(45) Date of Patent: Feb. 28, 2006

(54) METHOD OF REMOVING IRON OXIDE DEPOSITS FROM THE SURFACE OF TITANIUM COMPONENTS

(75) Inventors: Frank G. Belmonte, Norwood Park, IL (US); Kenneth J. Abrams, Naperville, IL (US); James Delaney, Jr., Bellwood, IL (US); Scott G. Kramer, Naperville, IL (US); David L. Sikkenga, Wheaton, IL (US)

(73) Assignee: BP Corporation North America Inc., Warrenville, IL (US)

(*) Notice: Subject to any disclaimer, the term of this patent is extended or adjusted under 35 U.S.C. 154(b) by 0 days.

(21) Appl. No.: 11/015,080

(22) Filed: Dec. 17, 2004

(65) Prior Publication Data

US 2005/0113603 A1 May 26, 2005

Related U.S. Application Data

(62) Division of application No. 10/255,339, filed on Sep. 26, 2002, now Pat. No. 6,852,879.

(60) Provisional application No. 60/327,464, filed on Oct. 5, 2001.

(51) Int. Cl.
*C23G 1/02* (2006.01)

(52) U.S. Cl. .............. 134/3; 134/2; 134/22.1; 134/26; 134/28; 134/30; 134/34; 134/35; 134/36; 134/41; 134/42

(58) Field of Classification Search .......... 134/2, 134/3, 22.1, 26, 28, 30, 34, 35, 36, 41, 42
See application file for complete search history.

(56) References Cited

U.S. PATENT DOCUMENTS

| | | | | |
|---|---|---|---|---|
| 2,959,555 A | * | 11/1960 | Martin et. al. | 134/3 |
| 3,041,215 A | * | 6/1962 | Jenkins et. al. | 148/247 |
| 3,468,774 A | * | 9/1969 | Kendall | 205/723 |
| 3,490,741 A | * | 1/1970 | Harriman et. al. | 510/253 |
| 3,696,040 A | * | 10/1972 | Mayo et al. | 507/267 |
| 3,725,224 A | * | 4/1973 | Kendall | 205/722 |

(Continued)

FOREIGN PATENT DOCUMENTS

GB 922507 A * 4/1963

(Continued)

OTHER PUBLICATIONS

Database WPI-Derwent Abstract XP0022223329 for JP51148709A, Dec. 20, 1976.*

(Continued)

*Primary Examiner*—Sharidan Carrillo
(74) *Attorney, Agent, or Firm*—Stephen L. Hensley

(57) ABSTRACT

Disclosed is a method and solvent composition capable of removing iron oxide deposits from the surface of titanium components without substantially damaging the underlying titanium component. Iron oxide deposits may be removed from the surface of a titanium component by contacting the titanium component with the solvent composition of the invention. The solvent composition may then be removed from contact with the titanium component to obtain a recyclable solvent composition which is recycled into repeated contact with the titanium component. The solvent composition comprises an aqueous mixture of an organic acid and a hydrohalide acid.

15 Claims, 1 Drawing Sheet

U.S. PATENT DOCUMENTS

| | | | |
|---|---|---|---|
| 3,794,523 A | * | 2/1974 | Thompson .................... 134/3 |
| 3,817,844 A | * | 6/1974 | Kendall ...................... 205/118 |
| 3,905,837 A | * | 9/1975 | Du Bois ...................... 148/264 |
| 3,957,529 A | * | 5/1976 | Alexander et al. ............. 134/3 |
| 4,174,290 A | * | 11/1979 | Leveskis ...................... 134/41 |
| 4,250,048 A | * | 2/1981 | Leveskis ...................... 510/264 |
| 4,623,399 A | * | 11/1986 | Frenier ......................... 134/3 |
| 5,463,113 A | * | 10/1995 | Yamamoto et al. ......... 562/414 |
| 5,510,521 A | * | 4/1996 | McGehee et al. ........... 562/414 |
| 5,621,007 A | * | 4/1997 | Gribkoff et al. ............ 514/387 |
| 5,723,656 A | * | 3/1998 | Abrams ...................... 562/412 |
| 5,925,786 A | * | 7/1999 | Isayama et al. ............. 562/412 |
| 6,137,001 A | * | 10/2000 | Broeker et al. ............. 562/413 |
| 2003/0098042 A1 | * | 5/2003 | Belmonte et al. .............. 134/3 |

FOREIGN PATENT DOCUMENTS

| | | | |
|---|---|---|---|
| GB | 1373230 | * | 11/1974 |
| WO | 0153246 | * | 7/2001 |

OTHER PUBLICATIONS

Publication, Centerline, vol. 5, No. 2, Summer 2001, pp. 6-8, 15-18, Mary Kay O'Connor Process Safety Cent.*

* cited by examiner

METHOD OF REMOVING IRON OXIDE DEPOSITS FROM THE SURFACE OF TITANIUM COMPONENTS

This application claims the benefit of U.S. Provisional Patent Application No. 60/327,464, filed Oct. 5, 2001, which is incorporated herein by reference. This application is a Divisional of Ser. No. 10/255,339, filed Sep. 26, 2002, now U.S. Pat. No. 6,852,879.

FIELD OF THE INVENTION

The present invention relates to a method and composition for removing iron oxide deposits from the surface of titanium components, and more particularly the use of such a method and composition to reduce or control buildup of iron oxide on titanium surfaces of process equipment in chemical manufacturing processes in which liquid process streams that may contain impurities in the form of dissolved iron or iron compounds are present and come in contact with such process equipment.

BACKGROUND OF THE INVENTION

Titanium components (defined as equipment and components of equipment made from, coated with or clad with titanium metal or otherwise having a surface of titanium metal) are useful in a variety of systems, processes and environments in which corrosion resistance is important. For example, titanium metal is used as a material of construction or fabrication for reaction vessels, liners and other reactor internals in chemical and other industrial processes that use or involve exposures to corrosive materials (including solvents, reactants, and by-products) or environments, such as an oxidizing environment. Titanium components also include heat exchangers due to titanium's corrosion resistance and resulting extended life of the equipment. Titanium components in the form of packing materials are often used in distillation columns and other separation devices used for gas-liquid separations involving corrosive materials. Although titanium components themselves are corrosion resistant, iron oxide deposits may form on surfaces of such titanium components when they are employed in systems or processes in which they come in contact with a source of iron, such as soluble iron or iron compounds which may be present as impurities in process streams. For example, titanium components are often integrated into systems which also employ relatively inexpensive stainless steel materials in areas where corrosion resistance is less important. These stainless steel materials may introduce dissolved iron into the system, which can accumulate on the surface of titanium components as iron oxide. In other systems, possible sources of iron include catalysts, liquid process streams and impurities.

The accumulation of iron oxide on a titanium component surface is often gradual but amounts of iron oxide accumulated over time can affect the usefulness of the titanium component. In the case of a titanium component in the form of a heat exchanger, for example, the accumulation of iron oxides on the surface of the titanium component may interfere with heat transfer. When titanium components are used in a distillation column as packing materials, a thin layer of iron oxides may form on the surface of the titanium packing when repeatedly exposed to dissolved iron, and it has been reported that "Accumulations of iron oxide . . . on titanium structured packing can promote or accelerate combustion of titanium. It may be appropriate to periodically remove accumulations of such materials through chemical or other means. However, if removal is accompanied by loss of titanium, it can create thinner metal, which may be sensitive to ignition" (*Centerline*, Vol. 5, No. 2, Summer 2001, pp. 6–8, 15–18, Mary Kay O'Connor Process Safety Center). This publication also reports that the presence of iron oxides "accelerated the oxidation of the titanium [packing] via a mechanism known as the Thermite Reaction in which the oxygen for combustion is taken from a less reactive metal oxide." Examples of thermite type reactions involving titanium metal and iron oxides may be represented by the following: $2FeO+Ti \rightarrow TiO_2+2Fe$; or $2Fe_2O_3+3Ti \rightarrow 3TiO_{2+4}Fe$.

Methods and compositions for removing oxide deposits are known from U.S. Pat. No. 3,957,529, which discloses a cleaning solvent comprising sulfuric acid and citric acid and its use to clean metal surfaces; U.S. Pat. No. 4,174,290, which discloses a method for removing metal oxides with a composition comprising an amine, a strong mineral acid and citric acid; and U.S. Pat. No. 4,250,048, which discloses a method for removing metal oxides with a composition comprising an ammonia derivative such as an amine, a strong mineral acid and an organic chelating agent for the metal oxides in an aqueous solution with a pH of about 0.5–3.0. U.S. Pat. No. 4,623,399 discloses a method of removing iron oxide scale from metal surfaces with a composition comprising a hydroxyethyl ethylenediamine triacetic acid and an organic acid such as formic acid. It also has been reported that ferrometal corrosion products are removed by use of citric acid or citric acid-tannin complexing agents with erythorbic acid reducing agents.

Although traditional methods and compositions are often useful for removal of iron oxides from various surfaces, their utility in particular applications can be limited in various respects, such as inadequate selectivity to iron oxides over other desirable metals that may be present and lack of compatibility or difficult integration with other aspects of the application. In the case of iron oxide deposits on surfaces of titanium components, selective removal, such that iron oxide is removed without substantial damage to or dissolving of the titanium component, can be especially important due to the relatively high cost of the titanium components.

It would, therefore, be desirable to provide a method and composition for removing iron oxide deposits from a titanium component without damaging the titanium component. In the case of titanium components used in chemical and other industrial processes, it would be particularly desirable to provide for removal or control of surface deposits of iron oxide on titanium components integrated with other aspects of the processes.

SUMMARY OF THE INVENTION

We have discovered a method and solvent composition capable of selectively removing iron oxide deposits from the surface of titanium components.

In accordance with the invention, the solvent composition comprises an aqueous solution of an organic acid and a hydrohalide acid.

In accordance with the invention, iron oxide deposits are selectively removed from a titanium component surface by contacting the titanium component with the solvent composition of the invention. Contacting with the solvent composition can be carried out in a single pass or by recycling the composition, including dissolved species, into one or more repeated contacts with the titanium component.

In accordance with another embodiment of the invention, iron oxide deposits which may be present are selectively removed from the surface of titanium component internals of a gas-liquid separation apparatus, such as a distillation column, by contacting the titanium component or components with a solvent composition comprising an aqueous solution of an organic acid and a hydrohalide acid in the substantial absence of molecular oxygen. Preferably in such an embodiment, aqueous organic acid is heated and introduced into the apparatus and circulated therein, and aqueous hydrohalide acid is added to the aqueous acid and the result is passed through the separation device. In a preferred embodiment, the organic acid is heated in contact with a heat exchange surface before being introduced into the separation device and before addition of substantial hydrohalide acid thereto, the heated acid is introduced into and circulated through the separation device in contact with its titanium component internals, the heat exchange surface is allowed to cool to a temperature low enough to avoid damage thereto on exposure to hydrohalide acid, the hydrohalide acid is added to the organic acid to form the solvent composition of the invention, and the solvent composition is passed through the separation device in contact with its internal titanium components.

The present invention is particularly useful for selectively removing solid iron oxides from the titanium component internals of a distillation column where the internals of the distillation column have been exposed to a source of iron (typically dissolved iron), and especially when also exposed to an oxidizing agent or environment, such as exposure to molecular oxygen.

BRIEF DESCRIPTION OF THE DRAWING

The single FIGURE of the drawing depicts an embodiment of the invention wherein iron oxide deposits may be removed from the titanium component internals of a distillation column.

DETAILED DESCRIPTION OF THE INVENTION

Figure 1:
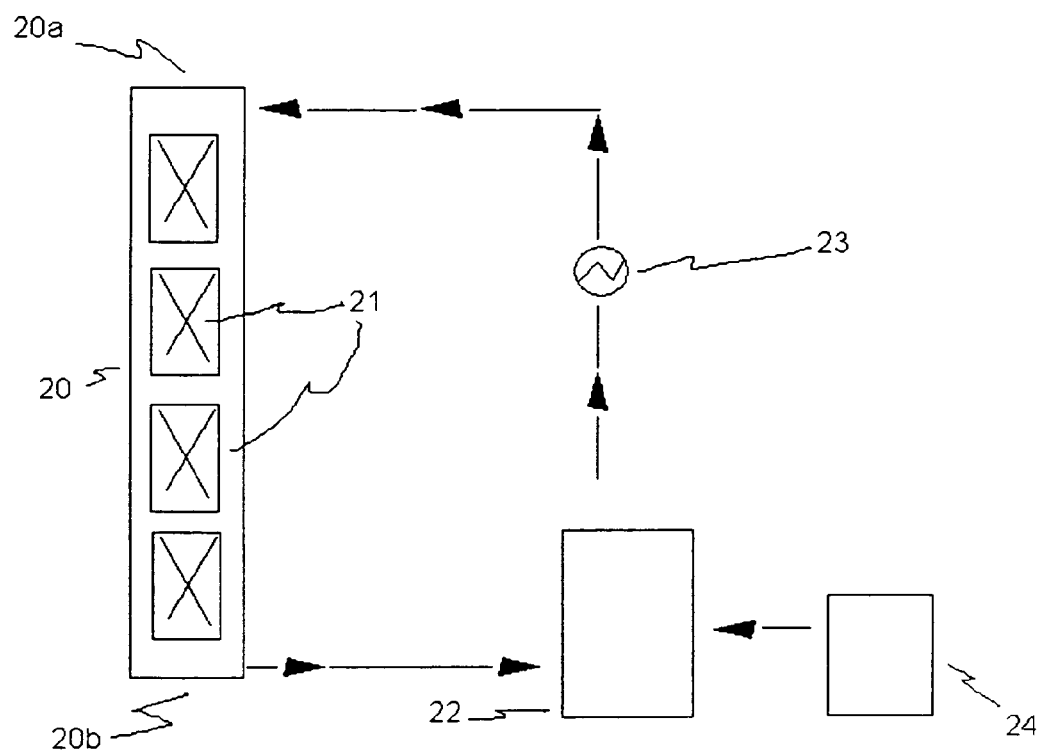

The invention is based, in part, on the discovery that iron oxide present in solid form on surfaces of titanium packings from a distillation column used for separation of water and acid in overhead gases generated in a liquid phase oxidation process for making aromatic carboxylic acids, and believed to have accumulated on the packings as a result of precipitation or deposition from vaporized process liquids or distillation reflux containing dissolved iron compounds, have a considerably higher content of iron (III) oxide, and particularly alpha $Fe_2O_3$, than iron (II) oxide. While iron-containing impurities dissolved in various liquid streams used in the process are believed to have a higher content of iron (II), the oxidizing agents, high temperatures and acidic and corrosive environment of the process promote oxidation of the more soluble iron (II) species dissolved in the liquid streams to less soluble iron (III) oxide, which tends to deposit on metal surfaces of process equipment. Titanium components find substantial use in such processes due to the severity of process conditions and materials, and accordingly, removal of iron oxide deposits which may form, and particularly iron (III) oxides, without damage to or dissolving titanium of the components, is important for process operation and equipment maintenance.

It is believed that the limited effectiveness of known methods and compositions to selectively remove iron oxides from titanium component surfaces may be attributed to iron (III) oxide. While iron (III) oxides as well as iron (II) oxide are often present in iron oxides formed on these titanium component surfaces, the former may predominate or be present in substantial amounts. Solvents that are effective for removal of deposited iron (II) oxide are less effective for dissolving deposited iron (III) oxide, and thus, removal of iron (III) oxides typically requires stronger solvents compared to iron (II) oxides. Although capable of completely or substantially removing iron oxides from a titanium component surface, stronger solvents also dissolve unacceptably high levels of titanium metal from the component and can cause damage to it. By use of the present invention's method and solvent composition, iron oxide deposits may be selectively removed from a titanium component surface even when substantial iron (III) oxide is present.

In accordance with one aspect, the invention provides a solvent composition useful for selectively removing iron oxides from titanium component surfaces comprising a hydrohalide acid, water, and an organic acid. Preferably, the solvent composition consists essentially of hydrobromic acid, water, and an organic acid. The solvent composition is capable of selectively removing substantial amounts of iron oxides, including all visible amounts of iron oxide deposit, from a titanium component surface. Removal of iron oxides is accomplished without or with only insubstantial removal of titanium from the titanium component.

In one embodiment, the solvent composition preferably has a titanium uptake capacity of no more than 2000 ppmw, more preferably no more than 500 ppmw, still more preferably no more than 100 ppmw, and even more preferably no more than 50 ppmw, and most preferably no more than 15 ppmw. Titanium uptake capacity refers to the amount of titanium metal which a given solvent composition is capable of dissolving on contact with a titanium metal sample at conditions under which the solvent is to be used. For preferred uses of the method and solvent composition of the invention, titanium uptake capacities are conveniently determined based on contact times of at least 48 hours at 80° C.

In another embodiment, the solvent composition can be used to remove all or substantially all visible iron oxide deposits from a titanium component surface while removing less than 1 wt. % of the total titanium metal in the titanium component. Preferably, visible iron oxide deposits from a titanium component surface are at least substantially removed while removing less than 0.5 wt. %, and still more preferably, less than 0.25 wt. %, of the total titanium metal in the titanium component.

The amounts of hydrohalide acid, water and organic acid present in the solvent composition are chosen such that the composition is capable of selectively removing iron oxide deposits from a titanium component surface. If too much hydrohalide acid is present, the solvent composition typically can dissolve an undesirable amount of the titanium in the titanium component. Accordingly, the amount of hydrohalide acid is preferably chosen such that the resulting solvent composition has a titanium uptake capacity of no more than 2000 ppmw, preferably no more than 500 ppmw, more preferably no more than 100 ppmw, and even more preferably no more than 50 ppmw, and even more preferably no more than 15 ppmw. Suitably, hydrohalide acid is present in the solvent composition in an amount between 0.5 to 20 wt. %, preferably from about 1 to about 10 wt. %, and more preferably from 4 to 8 wt. % of the total weight of the solvent composition. Preferably the hydrohalide acid is hydrobromic acid or hydrochloric acid, with hydrobromic acid being most preferred.

The amount of water present in the solvent composition is chosen such that the resulting solvent composition is effective for the selective removal of iron oxides from a titanium component surface. At relatively high levels of water, the solvent composition typically loses its effectiveness in removing iron oxide deposits. Water is suitably present in the solvent composition in an amount between 0.5 to 25 wt. % more preferably from 3 to 15 wt. %, and even more preferably from 4 to 8 wt. % of the total weight of the solvent composition.

After the appropriate amounts of hydrohalide acid and water have been chosen, the remainder of the solvent composition comprises primarily an organic acid. Preferably, the remainder of the solvent composition consists essentially of, and more preferably, consists of an organic acid.

In one preferred embodiment, the solvent composition comprises hydrohalide acid in an amount of 4–8 wt. %, water in an amount of 4–8 wt. %, with the remainder, ranging from about 84 to about 92 wt. %, being an organic acid.

The organic acid present in the solvent composition is an alkyl monocarboxylic acid having from 2 to 6 carbon atoms, benzoic acid, or a mixture thereof. Examples of suitable aliphatic carboxylic acids include acetic acid, propionic acid, butanoic acid and hexanoic acid. Acetic acid is preferably used as the organic acid because it is relatively inexpensive and readily recycled, i.e. easy to separate from other components.

For use in chemical or industrial processes in which process equipment comprising one or more titanium components contacts process streams or materials in which iron-containing impurities may be dissolved or present and in which reactants, solvents, products or other process materials or intermediates include an organic acid suitable for use in the solvent compositions used according to the invention, it is advantageous for efficient materials usage and recycle operations if the acid included in the solvent composition is the same as the process acid. For example, in the liquid phase oxidation of feed materials comprising an aromatic hydrocarbon to an aromatic acid using acetic acid as reaction solvent, use of acetic acid as the organic acid component of the invented solvent composition can eliminate or reduce redundancies in handling, separation, purification, recycle and other equipment and systems used for the acetic acid.

The amount of solvent composition used to selectively remove iron oxide deposits from a given titanium component surface may be determined by factors including iron uptake capacity of the solvent composition, the amount of iron present in the iron oxide deposits and extent to which iron is to be removed. Iron uptake capacity refers to the maximum amount of iron, calculated on the basis of elemental iron, which a given solvent composition is capable of dissolving when contacted with iron under conditions of use. As with titanium uptake capacity, for preferred uses of the solvent according to this invention, iron uptake determined based on contact times of at least 48 hours and temperatures of about 80° C. are convenient. Thus, for some applications it may be practical to determine the amount of solution of known iron uptake capacity to be used by approximating the amount of iron oxide deposits to be removed and the amount of iron contained in the iron oxides, and calculating the amount of solvent composition to be used.

The solvent composition of the invention is useful for selective removal of both iron (II) oxide (FeO), iron (III) oxides, including $Fe_2O_3$ in both alpha and gamma forms and FeO(OH), and the mixed oxide $Fe_3O_4$. It is particularly useful for selectively removing iron oxides comprising iron (III) oxides, and especially alpha $Fe_2O_3$, without dissolving substantial titanium from the titanium component. Iron (III) oxides typically are more difficult to selectively remove compared to iron (II) oxides. The solvent composition of the invention is capable of selectively removing iron oxide deposits from titanium components wherein the iron oxide deposits comprise primarily iron (III) oxide. Iron oxide deposits comprising at least 60 wt. % iron (III) oxide, and even as high as at least 90 wt. % are effectively removed or reduced according to the invention. Accordingly, the invention is particularly useful for reducing or controlling accumulation of iron oxide deposits on titanium components used in processes in which iron-containing impurities dissolved in process liquids or streams are exposed to the components in the presence of oxidizing reagents or atmospheres capable of oxidizing soluble iron (II) species to iron (III) oxides.

The solvent composition of the invention may be used to selectively remove iron oxide deposits formed on titanium component surfaces by contacting such titanium components with the solvent composition. Preferably for some applications, after the solvent composition has contacted the titanium component it is recycled and is again used to contact the titanium component in order to selectively remove additional iron oxide deposits. The solvent composition may be recycled in a batch-wise or continuous mode until the desired amount of iron oxide deposit has been removed. Within limits of a given solution's iron uptake capacity under conditions of use, each successive recycling removes an additional amount of the iron oxide deposits. Preferably, the solvent composition is recycled until all visible iron oxide deposits are removed from the titanium component while removing less than 1 wt. %, preferably less than 0.5 wt %, more preferably less than 0.25 wt. % of the total titanium in the titanium component.

When contacting the titanium component surface, the temperature of the solvent composition, whether fresh or recycled solvent that may also contain amounts of dissolved iron, should be chosen so that the solvent composition continuously remains homogenous and in the liquid phase but does not damage the titanium component or other equipment that may also be exposed to the solvent. Preferably, the temperature is sufficiently high to maximize the solubility of iron oxides deposits in the solvent composition or recycle thereof while sufficiently low so as to minimize dissolving the titanium of the titanium component. Preferably, the temperature should be sufficiently low so that less that 1 wt %, preferably less than 0.5 wt. %, even more preferably less than 0.25 wt. % of the total titanium in the titanium component is dissolved by the solvent composition upon removal of all visible iron oxide deposits from the titanium component. Temperatures below about 135° C. are preferred for solvent compositions containing hydrobromic acid because higher temperatures can lead to dissolution of undesirable levels of titanium metal. When contacting the titanium component, temperatures for the solvent composition or recycle thereof suitably range from about 10 to about 135° C., and preferably include between 10° C. to 125° C., more preferably between 55° C. to 100° C., and even more preferably between 70° C. to 90° C.

The pressure at which the titanium component is contacted with the solvent composition is any pressure which is suitable for a chosen temperature. Using above atmospheric pressures allows for higher temperature ranges for the solvent composition or recycle thereof. Using below atmospheric pressures requires the use of lower temperatures. Preferably, the pressure at which the titanium component is contacted with the solvent composition is about atmospheric.

The solvent composition or recycle thereof is preferably contacted with the titanium component surface in the substantial absence of molecular oxygen in order to avoid formation of potentially flammable mixtures. An atmosphere substantially free of molecular oxygen is conveniently provided by maintaining an atmosphere or flow of inert gas such as nitrogen around or within the titanium component to be treated.

Equipment, such as tanks, pumps, heat exchangers and piping, that may be used for mixing and heating the solvent composition and conveying it to or from a titanium component to be treated with the composition should be constructed from materials which themselves do not contain soluble forms of iron that might be dissolved by the composition, thereby reducing its iron uptake capacity before use. Stainless and other steels and other iron-containing metals are particularly disadvantageous in this regard. Titanium equipment is well suited for use as is equipment fabricated from polyethylene, polypropylene, polyvinylidine fluoride and other plastic resins that are resistant to attack by the solvent.

According to a more specific embodiment of the invention, an aqueous solvent composition comprising hydrogen halide acid and an aliphatic carboxylic acid of 2 to about 6 carbon atoms, benzoic acid or a combination thereof is used for removal or control of solid iron oxide deposits on titanium components, and particularly titanium components of distillation or other gas-liquid separation equipment, used in processes for the manufacture of aromatic carboxylic acids. In such processes, feed material comprising an alkyl aromatic compound or other oxidizable aromatic hydrocarbon, a catalyst composition, solvent comprising a monocarboxylic acid (e.g. acetic acid) and water are charged to a reaction vessel. Air is introduced into the reactor in order to provide a source of oxygen ($O_2$) necessary to complete a catalytic liquid phase oxidation which converts the alkyl aromatic to an aromatic acid. While air is a preferred source of molecular oxygen, pure oxygen, oxygen-enriched air and other sources also are suitable. The oxidation of aromatic hydrocarbon feed materials to product comprising Aromatic acid is conducted under oxidation reaction conditions. Temperatures in the range of about 120 to about 250° C. are suitable, with about 150 to about 230° C. preferred. Pressure in the reaction vessel is at least high enough to maintain a substantial liquid phase comprising feed and solvent in the vessel. This will vary with vapor pressures of the feed and solvents used in a given operation; by way of example, in the manufacture of terephthalic acid by oxidation of feed comprising para-xylene and solvent comprising acetic acid, suitable gauge pressures in the reaction vessel are about 0 to about 35 kg/cm$^2$ and preferably about 10 to about 20 kg/cm$^2$.

The oxidation produces water, at least a part of which typically is removed from the system. The oxidation is exothermic and the liquid reaction mixture normally is maintained in a boiling state for dissipation of heat of the reaction by vaporizing volatile components of the liquid mixture. This produces an overhead gas in the reaction vessel, which preferably is removed at the top of the vessel. This overhead gas comprises vaporized monocarboxylic acid, water vapor, oxygen ($O_2$), and gaseous by-products of the oxidation. When air is used as a source of molecular oxygen, nitrogen also is present in the overhead gas phase. In order to remove water while recycling other components (e.g. monocarboxylic acid) back to the reaction, the overhead gas is removed from the reactor to a separation device such as a distillation column or other reflux condenser. The separation device includes internal titanium components, such as packing or trays, due to corrosivity of the overhead gas. An example of titanium component packing materials are titanium packing materials, Titanium grade 1, 0.10 mm thickness, GEMPAK 2A commercially obtainable from Kock-Glitsch Inc. of Wichita, Kans.

In distillation, the internal titanium component packing materials facilitate the separation of monocarboxylic acid from water so that the majority of the acid condenses from the overhead gas and segregates to the bottom of the column and can be returned to the reaction vessel while a second gas phase comprising water vapor and uncondensable species is removed from the top of the column. Packings typically are in the form of thin sheets of titanium metal, which are typically corrugated, and disposed side-by-side in bundles within the column to provide a high surface area for heat exchange between an upwardly flowing vapor phase and downwardly flowing liquid phase comprising reflux and condensate. The distillation uses a water reflux, which can come from any source but preferably uses water from the system. For example the water removed from the top of the distillation column can be condensed and a portion of this condensate may be sent to the distillation column as reflux. The water reflux may also come from water which is used to wash or purify the aromatic acid product such as described in U.S. Pat. No. 5,723,656. Water reflux may be a source of dissolved iron resulting from contact with steel components of other equipment used in the liquid phase oxidation process or downstream process steps such as product recovery and purification. Examples of these steel components include piping, crystallizers, storage tanks, driers, centrifuges, filters, condensers, pumps, scrubbers, and the like. As described above, it is believed that the iron of the water reflux (thought to contain primarily $Fe^{+2}$) reacts with the oxygen of the overhead gas to form predominately iron (III) oxide on the surface of the packing materials. Internal packing materials exposed to the dissolved iron-containing water reflux and oxygen-containing overhead gas were analyzed by x-ray diffraction (XRD) and energy dispersive spectrometry (EDS), indicating that up to about 90 wt. % of the solid iron oxide deposits comprised iron (III) oxide with the remainder iron (II) oxide.

Iron oxide deposits are removed from internal titanium components of separation equipment, such as distillation column packings, used in processes for manufacture of aromatic acids by steps comprising discontinuing flow of overhead gases from the oxidation reactor into the separation device, and treating the device with the solvent composition of the present invention in the substantial absence of molecular oxygen. Discontinuing flow of reactor off gas to the separation device normally occurs during process shutdowns; however, in processes in which two or more separation systems are used, it also may be suitable to isolate one or more such system for treatment while one or more others continue operating. An atmosphere substantially free of oxygen is conveniently established in a distillation column or other separation device by purging or maintaining a flow of an inert gas such as nitrogen through the device. Oxygen levels during treatment should be maintained low enough to avoid formation of potentially flammable mixtures.

For use to remove iron oxide deposits from the internal titanium component surfaces of a distillation column or similar separation device (including surfaces of internal titanium packing materials), the solvent composition may be suitably introduced at the top of a distillation column and allowed to flow downwards and distribute throughout the column thereby contacting the column and the packing materials. Spraying or dripping the solvent from the top of the column onto the packing with a suitable spray or other liquid distribution means, including those normally used for introducing reflux liquid at the top of the column, are effective for introducing the solvent or its components into the column so that the liquid can flow downwardly through the column, typically by force of gravity, into contact with other packing surfaces. Preferably, before introduction to the column, the column and the solvent solution are purged with an inert gas such as nitrogen in order to remove reactive oxygen. After flowing downwards, solvent composition is collected at the bottom of the distillation column and can be disposed of or recycled to the top of the column, with addition of makeup fresh or recycle solvent as may be appropriate, by feeding and introducing it again to the top of the distillation column. The solvent solution may be recycled continuously through the column or other separation device or it can be recycled numerous times in a batch mode. Rinsing the titanium components with water after circulation of the solvent composition through the column or device is completed is beneficial for removal of solvent and residues thereof.

For use in treating a distillation column or other separation device, the solvent composition may be heated. Suitable temperatures at atmospheric pressure include between 10° C. to 135° C., preferably from about 30 to about 125° C., more preferably between 55° C. to 100° C., and even more preferably between 70° C. to 90° C. Contacting the titanium component internal components of the separation device is most preferably conducted at atmospheric pressure.

In a more specific embodiment of the invention, the solvent composition is contained by a reservoir, such as a holding tank, and is pumped from the reservoir to the top of a distillation column and allowed to flow downwards and distribute throughout. When the solvent composition reaches the bottom of the column it, including soluble iron compounds dissolved therein, is returned to the reservoir where the composition is collected and recycled, with makeup solvent or components, by pumping it back to the top of the distillation column.

In another specific embodiment, the solvent composition is created by sequentially introducing an organic acid, which may be aqueous and hydrohalide acid, preferably in aqueous form, to a distillation column. In this embodiment, the organic acid, preferably after heating, is introduced to the top of a distillation column and allowed to flow downwardly and distribute throughout the column thereby contacting the column and packing materials. The organic acid is introduced with a water content preferably less than 10 wt. %, more preferably less than 5 wt. %, and even more preferably less than 1 wt. %. Before its introduction to the top of the distillation column, both the organic acid and the column are purged with an inert gas such as nitrogen in order to remove reactive oxygen. When the organic acid reaches the bottom of the distillation column, it can be recycled for recirculation through the column by introducing it to the top of the distillation column. While the organic acid is passed through the column, hydrohalide acid is introduced to the distillation column or to a reservoir used to contain the organic acid, thereby forming the solvent composition in accordance with the invention. This solvent composition is then circulated, with recycle if desired, through the column. The hydrohalide acid is introduced as an aqueous solution preferably comprising water in an amount greater than 30 wt. %, more preferably greater than 40 wt. %, and even more preferably about 45 to 55 wt. %. The organic acid preferably is heated at a first temperature before introduction into the column, such as by contact with a heat exchange surface. Heating is discontinued and the heat exchange surface is allowed to cool sufficiently before addition of hydrohalide acid so that the acid does not damage the surface. After the hydrohalide acid is added, the resulting solvent composition cools to a second temperature. Typically, the second temperature is at least about 10° C. lower than the first temperature. The first temperature is preferably between 30° C. to 135° C., more preferably between 55° C. to 100° C., and even more preferably between 80° C. to 100° C. The second temperature is preferably between 30° C. to 110° C., more preferably between 55° C. to 100° C., and even more preferably between 70° C. to 90° C. The amounts of organic acid, hydrohalide acid and their respective water contents are chosen to achieve a desired resultant solvent composition after their sequential introduction to the column. The organic acid present in the resultant solvent composition is preferably greater than 50 wt. %, more preferably greater than 75 wt. %, and even more preferably from 70–90 wt. %. The hydrohalide acid present in the resultant solvent composition is preferably between 0.5 to 20 wt. %, preferably from about 1 to 10 wt. %, and more preferably from 4 to 8 wt. %. The water present in the resultant solvent composition is preferably between 0.5 to 25 wt. %, more preferably from about 3 to 15 wt. %, and more preferably from 4 to 8 wt. % of the total weight of the solvent composition.

The invention is further described with reference to the drawing. Shown in the drawing FIGURE is a distillation column 20, having a top at 20a and a bottom at 20b, with titanium component internal packing materials 21. In accordance with the invention, an organic acid, preferably acetic acid, is contained in a reservoir 22. Preferably the organic acid has no greater than 1 wt. % water. Both the column 20 and the reservoir 22 containing the organic acid are purged with an inert gas, preferably nitrogen. The organic acid is pumped to the top of the distillation column 20a using a pump (not shown). The organic acid is sprayed or dripped onto internals of the column at the top thereof and allowed to descend by force of gravity downwardly through column 20 and passes over, around and between packing materials 21. The organic acid is collected from the bottom 20b of the distillation column and returned to the reservoir 22 where it is recycled by pumping it back into the column 20. The organic acid is heated to a first temperature, most preferably between 80° C. to 100° C., by a heating apparatus 23, which is preferably a heat exchanger. Although heating apparatus 23 is shown in the drawing as disposed in the line feeding the top of the distillation column, any heating apparatus suitable for heating the organic acid can be used. Once the first temperature is achieved, there is preferably no further heating and, more preferably the heat exchange surface is allowed to cool sufficiently before addition of hydrohalide acid so that the acid is not heated in contact with the heat exchange surfaces to a temperature high enough to damage the surfaces. Hydrohalide acid, preferably hydrobromic acid, is then introduced from source 24 and pumped into reservoir 22 to mix with the organic acid thereby forming the solvent composition of the invention. Preferably, the total amount of hydrohalide acid is added slowly over an extended period of time (e.g. 1–4 hours or more) in order to promote equilibrium mixing with the organic acid. The solvent composition is then circulated to and through the distillation column 20. Typically the solvent composition is circulated for a period of from 1 to 48 hours. For best results, all of the surfaces of the components which come in contact with the solvent composition should comprise titanium or other material which is substantially insoluble in the solvent composition.

The organic acid originally contained in 22 is preferably a mixture comprising water and primarily organic acid wherein the water content of the mixture is preferably less than 10 wt. %, more preferably less than 5 wt. %, and even more preferably less than 1 wt. %. The hydrohalide acid originally contained in source 24 is preferably an aqueous solution preferably comprising water in an amount greater than 30 wt. %, more preferably greater than 40 wt. %, and even more preferably about 45 to about 55 wt. %. Most preferably the hydrohalide acid is aqueous 48 wt. % hydrobromic acid.

In a specific embodiment of the invention, titanium components such as packing materials are treated with the solvent composition to control iron oxide deposits on surfaces of the components so that deposits do not accumulate to levels that may adversely affect the titanium components. Thus, treatment according to the invention can be included in maintenance procedures used during shutdowns or other interruptions of processes in which equipment with titanium components is used. Thickness of solid iron oxide deposits on surfaces of titanium components can easily be maintained at less than 300 microns, and preferably less than 100 microns, more preferably less than 50 microns, and even at less than 25 microns by treatment according to the invention, including repeated treatments as may be appropriate to equipment used in a given process under its particular conditions.

Accordingly, for example, the method and solvent composition of this invention may be integrated with a process for the manufacture of an aromatic carboxylic acid. In general, the method and solvent composition of the present invention may be integrated with a process for the manufacture of an aromatic carboxylic acid comprising the steps of oxidizing an aromatic compound to an aromatic carboxylic acid in a liquid phase reaction mixture comprising the aromatic compound, water, a low molecular weight monocarboxylic acid solvent, an oxidation catalyst and a source of molecular oxygen, under reaction conditions, to produce an aromatic acid product and a gas phase comprising water vapor, unreacted molecular oxygen and gaseous low molecular weight monocarboxylic acid solvent; removing all or part of the gas phase from the reaction zone to a separation device having internal titanium components; and separating the gas phase in the separation device into a liquid phase comprising monocarboxylic acid solvent and a second gas phase comprising water vapor. The oxidation is carried out in a reaction zone, such as provided by a closed, pressure-rated stirred tank reactor or vessel, with sufficient volume to accommodate the liquid reaction mixture and the gaseous phase, with the latter most commonly present as an overhead gas phase above the liquid level in the reaction zone.

In a specific embodiment of such a process, a feed material comprising para-xylene is oxidized to product comprising terephthalic acid using a solvent comprising acetic acid and air as a source of molecular oxygen. Catalysts for such processes typically comprise a heavy metal component, and most preferably cobalt, manganese and a source of bromine.

The gas phase is removed from the reaction zone to the separation device, which preferably is, or includes, a distillation apparatus with titanium packings for separation of the gas phase into liquid and gaseous phases. Monocarboxylic acid in the liquid phase is conveniently recycled to the reaction zone. The remaining gas phase can be condensed to recover water for other uses, used for heat exchange or directed to a suitable energy recovery device, such as an expander.

Examples of processes for the manufacture of an aromatic carboxylic acid in which the present invention can be utilized are disclosed in U.S. Pat. No. 5,925,786; U.S. Pat. No. 5,723,656; U.S. Pat. No. 5,510,521; U.S. Pat. Nos. 5,463,113; 5,621,007; and British Patent 1373230; all of which are incorporated by reference.

The separation device is treated to remove solid iron oxide deposits which may be present on a surface of its internal titanium components by discontinuing removal of the gas phase from the reaction zone to the separation device and separation of the gas phase therein, and passing through the device in contact with the titanium component surfaces and in the substantial absence of molecular oxygen the aqueous solvent composition according to the invention. Discontinuing the removal and separation steps can be effected by any suitable means, such as in conjunction with process shutdowns or interruptions. As described above, in processes conducted with multiple separation devices it may also be suitable to bypass or isolate one or more of such device, which, after evacuation of process materials, can be treated while one or more other devices continues operating. Evacuation of process materials from the separation device and rinsing the device, for example with caustic, water, or both in sequence, preferably is conducted before treating the device with solvent composition for removal of iron oxide deposits that may be present. Purging the device with inert gas before treating with the solvent composition also is beneficial toward maintaining an atmosphere substantially free of molecular oxygen.

As will be appreciated, passage of the solvent composition or its components through the separation device is carried out in the substantial absence of molecular oxygen to avoid creation of potentially flammable mixtures within the device. An atmosphere substantially free of molecular oxygen refers to presence of molecular oxygen at low enough levels, taking into account organic species present during treatment with the solvent composition, iron oxide levels that may be present, and conditions such as temperature and pressure, to avoid formation of a flammable vapor mixture in the device. Persons skilled in the art can determine such levels by reference to standard sources concerning flammable gas mixtures. Most conveniently, a substantial absence of molecular oxygen is maintained in the separation device by purging the device with an inert gas, such as nitrogen, before introducing the solvent composition or its components, by maintaining a flow of inert gas through the device during treatment, or both.

As described above, solvent composition can be formulated before being introduced to the separation device or its components can be added separately. In a particular embodiment, passage of the solvent composition through the separation device is accomplished by passing the organic acid component, optionally with water, through the device in the substantial absence of molecular oxygen, adding hydrohalide acid and water to the organic acid in the substantial absence of molecular oxygen to obtain the solvent composition; and passing the solvent composition through the device in contact with the titanium component in the substantial absence of molecular oxygen. Best results in such an embodiment are attained when the organic acid is heated to a first temperature, preferably of about 40 to about 125° C.

and passed through the device substantially at the first temperature, after which the aqueous hydrohalide acid at a lower temperature is added to the organic acid, such that the acids combine to form the solvent composition at a lower temperature and are passed through the device into contact with the titanium components in the substantial absence of molecular oxygen. Preferred solvent compositions for such use contain about 4 to about 8 wt. % hydrohalide acid, about 5 to about 15 wt. % water and about 77 to about 91 wt. % organic acid, with hydrobromic and acetic acids being most preferred as the hydrohalide and organic acids, respectively.

In processes in which the low molecular weight monocarboxylic acid reaction solvent also is a material suitable as the organic acid component of the solvent composition according to the invention, use of the same acid as both the reaction solvent and solvent composition component can provide further advantages. For example, in the manufacture of terephthalic acid by oxidation of a para-xylene feed in acetic acid as the reaction solvent, use of acetic acid as the organic acid of the solvent composition for treating the separation device can facilitate solvent handling and purification. Removal of solvent with dissolved iron compounds after passage through the separation device, and recovery of organic acid therefrom, such as by distillation, can be employed to allow recycle of the organic acid for use as reaction solvent. Conversely, liquid monocarboxylic acid solvent recovered as a result of separation of the gas phase removed from the reaction zone can be recycled for use as the organic acid component of the solvent composition for treating the titanium internal components of the separation device.

The following examples illustrate, but do not limit, the invention.

EXAMPLE 1

Water, acetic acid, and HBr were charged into a round bottom four-necked flask equipped with a condenser and stirrer in the following amounts: 13 g water, 85 g acetic acid, and 2 g aqueous HBr (48 wt. % HBr). This yielded a solvent composition of 14.04 wt. % water, 85 wt. % acetic acid, and 0.96 wt. % HBr. The solution was purged gas by bubbling nitrogen gas into the solution in the flask. While stirring, 0.30 g of iron (III) oxide was charged into the flask. The contents of the flask were heated and maintained at 80° C. under a constant nitrogen gas purge. After 24 hours under these conditions, undissolved iron (III) oxide was observed. In order to recover undissolved iron (III) oxide, the flask contents were filtered hot (85° C.) at reduced pressure (15 in. Hg, 381 mm Hg) using a vacuum flask, a filtering funnel, and 5.5 cm WHATMAN filter paper #1 (Cat. No. 1001.055) from Whatman International Ltd. of the United Kingdom. The amount of recovered iron (III) oxide was 0.025 g, corresponding to 8.63 wt. % of the 0.30 g of iron (III) oxide that was initially charged.

EXAMPLES 2–6

The procedures of Example 1 were substantially repeated but with the variations reported in Table 1.

Results of Examples 1–6 are summarized in Table 1 below and show that various solvent compositions comprising water, acetic acid, and hydrobromic acid were effective for dissolving iron (III) oxide.

TABLE 1

| Ex | HBr (wt %) | H2O (wt %) | $Fe_2O_3$ (g) | Temp (° C.) | Time (hr) | Undissolved $Fe_2O_3$ (g/wt %) | 100%-wt % Undissolved $Fe_2O_3$ |
|---|---|---|---|---|---|---|---|
| 1 | 0.96 | 14.04 | 0.30 | 80 | 24 | 0.025/8.63 | 91.37 |
| 2 | 0.96 | 14.04 | 0.30 | 108 | 52 | 0.0167/5.57 | 94.43 |
| 3 | 2.88 | 12.12 | 0.30 | 108 | 0.2 | Nil | ~100 |
| 4* | 2.88 | 12.12 | 0.60 | 102 | 10.5 | 0.0167/2.73 | 97.27 |
| 5 | 2.88 | 12.12 | 0.90 | 108 | 10.25 | 0.0415/4.61 | 95.39 |
| 6 | 2.88 | 12.12 | 1.5 | 108 | 15.5 | 0.101/6.73 | 93.27 |

*The contents of the flask were not stirred in this example.

EXAMPLE 7

Water, acetic acid, and HBr were charged to a round bottom, four necked flask equipped with a condenser and stirrer in the following amounts: 18.0 g water, 170.0 g acetic acid, and 12.0 g aqueous HBr (48 wt. % HBr). This yielded a solvent composition of 12.12 wt. % water, 85 wt. % acetic acid, and 2.88 wt. % HBr. The solution was purged with nitrogen as in the prior examples. While stirring, 3.0 g of iron (III) oxide was charged into the flask and heated and maintained at 30° C. About a 3 gram sample of the solvent composition was taken. The contents of the flask were then stirred and maintained at temperature of 30° C. Samples of the solvent composition were taken at two-hour intervals after stirring was stopped and undissolved iron (III) oxide was allowed to settle. After each sampling, stirring of the flask contents was resumed. Samples were taken over an eight-hour period. All samples were analyzed for Fe content by Inductively-Coupled Plasma Spectrometry (ICP). Results, designated 7a, are summarized in Table 2. Undissolved iron (III) oxide remaining after the sampling period was filtered hot (85° C.) at reduced pressure (15 in. Hg, 381 mm Hg) using a vacuum flask, a filtering funnel, and 5.5 cm WHATMAN filter paper #1. The amount of undissolved iron (III) oxide was recorded in grams and divided by 3.0 g (initial amount of iron charged) to calculate the wt. % undissolved iron (III) oxide.

This procedure was repeated except the solution was maintained at 60° C. while stirring. Results, designated 7b, are reported in Table 2.

The procedure was repeated again but with a 1.5 g iron (III) oxide sample and the temperature maintained at 108° C. for 15.5 hours while stirring. Results, designated 7c, are reported in Table 2 and also discussed after the table.

The results for examples 7a–7c illustrate effects of time and temperature on effectiveness of the solvent composition for dissolving iron (III) oxide.

TABLE 2

| Ex | Temp. (° C.) | Time (hrs) | Fe by ICP (ppm) | Undissolved $Fe_2O_3$ at 8 hrs. (g) | Undissolved $Fe_2O_3$ at 8 hrs. (wt. %) | Dissolved $Fe_2O_3$ at 8 hrs. (wt. %) |
|---|---|---|---|---|---|---|
| 7a | 30 | 0 | 359 | 1.438 | 47.93 | 52.07 |
|    |    | 2 | 3430 |      |       |       |
|    |    | 4 | 3810 |      |       |       |
|    |    | 6 | 4110 |      |       |       |
|    |    | 8 | 4250 |      |       |       |
| 7b | 60 | 0 | 2330 | 1.0869 | 36.23 | 63.77 |
|    |    | 2 | 4830 |      |       |       |
|    |    | 4 | 4220 |      |       |       |

TABLE 2-continued

| Ex | Temp. (° C.) | Time (hrs) | Fe by ICP (ppm) | Undissolved Fe₂O₃ at 8 hrs. (g) | Undissolved Fe₂O₃ at 8 hrs. (wt. %) | Dissolved Fe₂O₃ at 8 hrs. (wt. %) |
|---|---|---|---|---|---|---|
|    |     | 6 | 5770 |       |       |       |
|    |     | 8 | 5680 |       |       |       |
| 7c | 108 | 0 | 5090 | 0.293 | 19.53 | 80.47 |
|    |     | 2 | 6715 |       |       |       |
|    |     | 4 | 7930 |       |       |       |
|    |     | 6 | 7910 |       |       |       |
|    |     | 8 | 8490 |       |       |       |

After 15.5 hours under the conditions of Example 7c, undissolved iron oxide was observed and was recovered by filtering the contents of the flask hot (85° C.) at reduced pressure (15 in. Hg, 381 mm Hg) using a vacuum flask, a filtering funnel, and 5.5 cm WHATMAN filter paper #1. The amount of recovered iron (III) oxide was 0.101 g, which corresponds 6.73 wt. % of the 1.5 g of iron (III) oxide that was initially charged.

EXAMPLE 8

A 100 g sheet of corrugated titanium packing material designated GEMPACK 2A, Titanium grade 1, having a thickness of 0.10 mm was obtained from Kock-Glitsch Inc. The sheet was cut into one inch (2.54 cm) square samples. Acetic acid (1575 g) and aqueous, 48 wt. % HBr (225 g) were charged to a two liter container equipped with a condenser and stirrer. This yielded a solvent composition of 6.5 wt. % water, 87.5 wt. % acetic acid, and 6.0 wt. % HBr. The solution was purged with nitrogen as in the previous examples. While stirring, all of the square samples were charged into the container and the contents were heated and maintained at 80° C. while maintained under a constant nitrogen purge. A sample (about 5 g) of the solvent composition was taken. The contents of the container were then stirred and maintained at temperature of 80° C. under constant nitrogen purge. Samples (about 5 g) of the solvent composition were taken after 1 hour, 2 hours, 4 hours, 8 hours, 24 hours, and 48 hours. Before each sampling, stirring was stopped and the contents of the container were allowed to come to rest. After each sampling, stirring of the flask contents was resumed. All samples were analyzed to determine the amount of dissolved titanium by ICP. After 48 hours only 9.9 ppmw of titanium was dissolved in the solvent composition, which corresponds to 0.018 wt. % of the original 100 g sample of titanium packing material. Results of sampling at different times are summarized in Table 3 and show that the solvent composition comprising water, acetic acid, and hydrobromic acid did not substantially dissolve titanium metal.

TABLE 3

| Time (hrs) | Amount of Dissolved Titanium (ppmw) | Amount of Dissolved Titanium (wt %) |
|---|---|---|
| 0 | 0.2 | 0.00002 |
| 1 | 1.9 | 0.00019 |
| 2 | 3.5 | 0.00035 |
| 4 | 4.4 | 0.00044 |
| 8 | 6.5 | 0.00065 |
| 24 | 7.9 | 0.00079 |
| 48 | 9.9 | 0.00099 |

EXAMPLES 9–13 AND COMPARATIVE EXAMPLE 14

Titanium samples with iron oxide deposits were used in Examples 9–13. The titanium samples had a layer of iron oxide deposits in the range of 15 μm to 25 μm as determined by scanning electron microscopy (SEM). About 90 wt. % of the iron oxide deposits was iron (III) oxide as determined by x-ray diffraction (XRD) and energy dispersive spectrometry (EDS). The titanium samples were obtained from packing materials which had been used in a distillation column of a commercial-scale unit for manufacture of terephthalic acid by liquid phase oxidation of a para-xylene feed. The distillation column had been operated on top of a liquid phase oxidation reactor and used to separate acetic acid from water in a reactor off-gas removed from the reactor into the column. The packing materials were corrugated titanium packing materials, Titanium grade 1, 0.10 mm thickness, similar to the unused sample in Example 8. Examples 9–10 show that solvent compositions comprising water, acetic acid, and hydrobromic acid were effective for removing iron oxide deposits from the used titanium packing material. Examples 11a–11c show how the amount of iron in solution affected the ability of the solution to remove an iron oxide coating from the surface of the titanium component. The solution from 11a with little or no iron present was very effective. However, the solution from 11c that had significantly more iron and was near its maximum iron uptake quantity did not effectively remove the iron oxide coating. Example 12 shows the use of hydrochloric acid in place of hydrobromic acid. Example 13 shows the use of propionic acid in place of acetic acid. Comparative Example 14 shows that a common solvent for removing iron oxide, oxalic acid dihydrate, also dissolved significant titanium.

EXAMPLE 9

Water (218.75 g), acetic acid (2125 g), and aqueous 48 wt. % HBr (156.25 g) were mixed to obtain a solvent composition of 12 wt. % water, 85 wt. % acetic acid, and 3 wt. % HBr. A 1200 ml column equipped with a condenser and band heaters was erected laterally and was filled with the solvent composition. A nitrogen atmosphere was maintained in the headspace over the liquid level in the column. The solvent composition was then heated and maintained at 60° C. in the column. A sample cut from the titanium packing material with iron oxide deposits was weighed to record an initial weight and was supported horizontally in a funnel. The wash solution was allowed to flow from the column and over the sample at an average flow rate of 210 ml/hr for 20 hours. The temperature at which the solvent composition contacted the sample was 45° C. and was measured by placing a thermocouple in line of the solvent composition liquid flow at the point of contact with the sample. After 20 hours, the sample was removed, dried and weighed. The weight loss calculated from the initial and final weights in this example, referred to as 9a, was 8.05 wt. %.

The procedure of Example 9a was repeated but at a solvent temperature in the column of 30° C., contact temperature of 25° C. and for 22.5 hours. The calculated weight loss for this example, referred to as 9b, was 3.33 wt. %.

After sampling in 9b, heating was continued, with average flow rate of 215 ml/hr., and a sample was taken after heating for a total of 34 hours. The calculated weight loss for the sample, referred to as 9c, was 4.27 wt. %.

After sampling in 9c, heating was again continued, with an average flow rate of 212 ml/hr. A sample, designated 9d, was taken after the total heating time was 41 hours. The calculated weight loss for this example, referred to as 9d, was 4.81 wt. %.

Results of these examples are reported in Table 4. After contact with the solvent compositions, visual observation of the samples from 9a –d revealed decreased levels of iron oxide on the sample surfaces with no or negligible damage to the titanium surfaces, indicating weight losses were attributable essentially to solid iron oxide dissolved from the sample surfaces.

TABLE 4

| Ex. | Temp. (° C.) Column | Temp. (° C.) Contact | Flow Rate (ml/hr) | Time (hrs) | Weight Loss (wt %) |
|---|---|---|---|---|---|
| 9a | 60 | 45 | 210 | 20 | 8.05 |
| 9b | 30 | 25 | 210 | 22.5 | 3.33 |
| 9c | 30 | 25 | 215 | 34 | 4.27 |
| 9d | 30 | 25 | 212 | 41 | 4.81 |

EXAMPLE 10

Water (104.56 g), acetic acid (1015.75 g), and aqueous 48 wt. % HBr (74.68 g) were mixed to obtain a solvent composition of 12 wt. % water, 85 wt. % acetic acid, and 3 wt. % HBr. A 1200 ml column equipped with a condenser and band heaters was erected laterally and was filled with the solvent composition. The solvent was heated to and maintained at 80° C. in the column. A sample cut from the iron oxide-coated titanium packing material was weighed to record an initial weight and was supported horizontally in a funnel. The wash solution was allowed to flow from the column and over the sample at an average flow rate of 208 ml/hr. The temperature at which the solvent composition contacted the sample was 59° C. and was measured as in Example 9. At intervals of 4 hours, 11.5 hours, 18.25 hours, and 21.25 hours the flow was stopped and the sample was removed from the funnel and weighed to determined weight loss. After weighing, the sample was returned to the funnel and the process was resumed. Weight loss at each time interval is shown in Table 5. After 21.25 hours, no visible iron oxide deposits were observed on the titanium sample.

TABLE 5

| Time (hrs) | Weight Loss (wt %) |
|---|---|
| 4 | 5.30 |
| 11.5 | 5.84 |
| 18.25 | 18.04 |
| 21.25 | 19.19 |

The high percentage weight losses at 18.25 and 21.25 hours were attributable to heavy iron oxide coatings on the sample material.

EXAMPLE 11

Acetic acid (87.5 g) and 48 wt. % HBr (12.5 g) were charged to a round bottom four necked flask equipped with a condenser and stirrer. This yielded a solvent composition of 6.5 wt. % water, 87.5 wt. % acetic acid, and 6.0 wt. % HBr. The solution was purged with nitrogen gas as in previous examples. While stirring, an iron oxide-coated sample of the titanium packing material weighing 0.2473 g was charged into the flask. The contents of the flask were heated, stirred, and maintained at 80° C. under a constant nitrogen gas purge. After 48 hours, the sample was shiny and visually free of iron oxide deposits. The solution comprised 0.7 ppm of dissolved titanium and 143 ppm of dissolved iron as determined by ICP.

In another trial, water (2.42 g), acetic acid (87.5 g), aqueous, 48 wt. % HBr (7.8465 g), and $FeBr_3$ (2.754 g) were charged into a round bottom four-neck flask equipped with a condenser and stirrer. This yielded a solvent composition of 6.5 wt. % water, 87 wt. % acetic acid, 3.7 wt. % HBr, and 0.52 wt. % iron. The solution was purged with nitrogen gas as in previous examples. While stirring, a sample of the iron oxide coated packing (0.3312 g) was charged to the flask. The contents of the flask were heated, stirred, and maintained at 80° C. under a constant nitrogen gas purge. After 48 hours, the sample was shiny and visually free of iron oxides. The solution comprised 0.8 ppm of dissolved titanium and 5300 ppm of dissolved iron as determined by ICP.

In another trial, water (5.586 g), acetic acid (87.5 g), aqueous 48 wt. % HBr (1.758 g), and $FeBr_3$ (6.356 g) were charged into a round bottom four necked flask equipped with a condenser and stirrer. This yielded a solvent composition of 6.4 wt. % water, 86.5 wt. % acetic acid, 0.83 wt. % HBr, and 1.2 wt. % iron. The solution was purged with nitrogen gas as in the previous trials. While stirring, a sample of the iron oxide coated titanium packing (0.3125 g) was charged to the flask. The contents of the flask were heated, stirred, and maintained at 80° C. under a constant nitrogen gas purge. After 48 hours, iron oxide deposits were still visible on the sample but the solution contained 0.6 ppm of dissolved titanium and 12160 ppm of dissolved iron as determined by ICP.

EXAMPLE 12

Water, acetic acid, and aqueous HCl were charged to a 250 ml round bottom four neck flask equipped with a condenser and stirrer in the following amounts: 6.892 g water, 85 g acetic acid, and 8.108 g aqueous HCl (37 wt. % HCl). This yielded a solvent composition with 12.0 wt. % water, 85 wt. % acetic acid and 3.0 wt. % HCl. The stirred solvent was purged with nitrogen and heated to 60° C. A sample of the titanium packing with iron oxide coating was added to the hot solution. After six hours under these conditions, the titanium sample was shiny and visually appeared to have no iron oxides. The sample was weighed to determine a recorded weight loss of 0.0129 g, which corresponds to 8.6 wt. % based on initial sample weight.

EXAMPLE 13

Water, propionic acid, and HBr were charged to a 250 ml round bottom four neck flask equipped with a condenser and stirrer in the following amounts: 12.0 g water, 85.0 g propionic acid and 6.0 g aqueous HBr (48 wt. % HBr). This yielded a solvent composition containing 14.68 wt. % water, 82.52 wt. % propionic acid, and 2.80 wt. % HBr. The stirred solution was purged with nitrogen and heated to 60° C. A sample of the titanium packing coated with iron oxide was added to the hot solution. The sample was removed and weighed at 8, 32, 40, and 56 hours to determine the rate of iron oxide removal. After 56 hours, 0.0071 g or 4.21 wt. % (75.53 wt. % of 0.0094 g total coating weight) was removed from the titanium packing. The solution was heated to 80° C. and the titanium sample was contacted at this condition for another 2.5 hours and then weighed. The titanium packing was free of iron oxide visibly. At the end of the additional 2.5 hours, the sample was free of visible iron oxide and weight loss was 0.0094 g, which corresponds to 5.58 wt. % of the initial sample. Results of the sampling in this example are reported below.

| Time (hours) | Temp (° C.) | $Fe_2O_3$ (grams) | Weight Loss Wt. % |
|---|---|---|---|
| 8 | 60 | 0.0041 | 2.43 |
| 32 | 60 | 0.0058 | 3.44 |
| 40 | 60 | 0.0062 | 3.68 |
| 56 | 60 | 0.0071 | 4.21 |
| Temperature was increased to 80° C. | | | |
| 1.5 | 80 | 0.0088 | 5.20 |
| 2.5 | 80 | 0.0094 | 5.58 |

COMPARATIVE EXAMPLE 14

Water (17,660 g) and 99% purity oxalic acid dihydrate (883 g) were charged to a 19 liter glass tank with nine port holes and equipped with a condenser and stirrer to provide a solvent composition containing 96.60 wt. % water and 3.40 wt. % oxalic acid. Three new titanium corrugated packing bundles (GEMPACK 2A, Titanium grade 1, 0.10 mm thickness commercially obtained from Kock-Glitsch Inc.) were individually weighed and recorded. Each titanium packing bundle was made up of six pre-cut sheets that weighed between 5.0–6.3 g. The bundles were labeled Bundle #1, Bundle #2 and Bundle #3. The aqueous oxalic acid solution was stirred and heated to 80° C. The titanium bundles were suspended in the hot solution and periodically weighed. The titanium weight loss of Bundle #1 was 3.92 g (11.13 wt. %) after 3 hours and 5 minutes. The titanium weight loss of Bundle #2 was 8.704 g (26.12 wt. % titanium) after 5 hours and 40 minutes. The titanium weight loss of Bundle #3 was slightly below 26 wt. % after 5 hours and 40 minutes. After an additional 1.5 hours in the solvent, a weight loss of slightly above 26 wt. % for Bundle #3 was recorded. A new batch of solvent (17660 g of water and 883 g of oxalic acid dihydrate) was made and heated to 80° C. Bundle #3 was suspended in the hot solution for an additional 4 hours and 53 minutes. Bundle #3 weight loss after that period was 17.769 g (50.47 wt. %).

Iron oxide coated titanium packing samples were also tested with the oxalic solution but removal of iron oxides was accompanied by substantial dissolving of titanium metal.

As many different embodiments of this invention may be made without departing from the spirit and scope thereof, it is to be understood that the invention is not limited to the specific embodiments thereof described herein.

We claim:

1. A method for treating a gas-liquid separation device comprising an internal titanium component to control accumulation of deposits of solid iron oxide on a surface of the titanium component comprising the steps of
   (a) introducing to the separation device an organic acid comprising an alkyl monocarboxylic acid having 2 to 6 carbon atoms, benzoic acid or mixture thereof at a first temperature in the range of about 30 to about 125° C. and passing the organic acid through the separation device in the absence of molecular oxygen levels forming a flammable mixture;
   (b) adding to the organic acid in the absence of molecular oxygen levels forming a flammable mixture an aqueous hydrohalide acid at a temperature which is lower than the first temperature to obtain an aqueous solvent composition at a second temperature which is lower than the first temperature; and
   (c) contacting the titanium component with the solvent composition in the separation device in the absence of molecular oxygen levels forming a flammable mixture.

2. The method of claim 1 wherein the organic acid is an aqueous alkyl carboxylic acid of 2 to 6 carbon atoms.

3. The method of claim 1 wherein the organic acid is acetic acid.

4. The method of claim 1 wherein the organic acid is benzoic acid.

5. The method of claim 1 wherein the hydrohalide acid is hydrobromic acid.

6. The method of claim 1 wherein the aqueous hydrohalide acid contains at least about 30 wt. % hydrobromic acid.

7. The method of claim 1 comprising an additional step comprising maintaining a flow of an inert gas through the separation device.

8. The method of claim 1 wherein the gas-liquid separation device comprises a distillation column and an internal titanium component comprises titanium packings or trays.

9. The method of claim 1 wherein the gas-liquid separation device comprises a reflux condenser and an internal titanium component comprises titanium packings or trays.

10. The method of claim 6 wherein the organic acid and the hydrohalide acid are introduced in amounts such that the solvent composition contains between 0.5 to 20 wt. % hydrohalide acid and between 0.5 to 25 wt. % water.

11. The method of claim 8 wherein the organic acid comprises acetic acid.

12. The method of claim 9 wherein the organic acid comprises acetic acid.

13. The method of claim 9 wherein the organic acid comprises hydrobromic acid.

14. The method of claim 10 wherein the second temperature is between 55° C. to 100° C.

15. The method of claim 11 wherein the hydrohalide acid comprises hydrobromic acid.

* * * * *